March 24, 1964 R. S. MOORE Plant Pat. 2,386

ROSE

Filed Jan. 12, 1962

WITNESS
Jeanette Nunn Copley

INVENTOR
RALPH S. MOORE
ATTORNEYS
E. Wolff and Son

United States Patent Office

Plant Pat. 2,386
Patented Mar. 24, 1964

2,386
ROSE

Ralph S. Moore, 2519 E. Mineral King, Visalia, Calif.

Filed Jan. 12, 1962, Ser. No. 165,977
1 Claim. (Cl. Plt.—5)

Figures 1, 2:
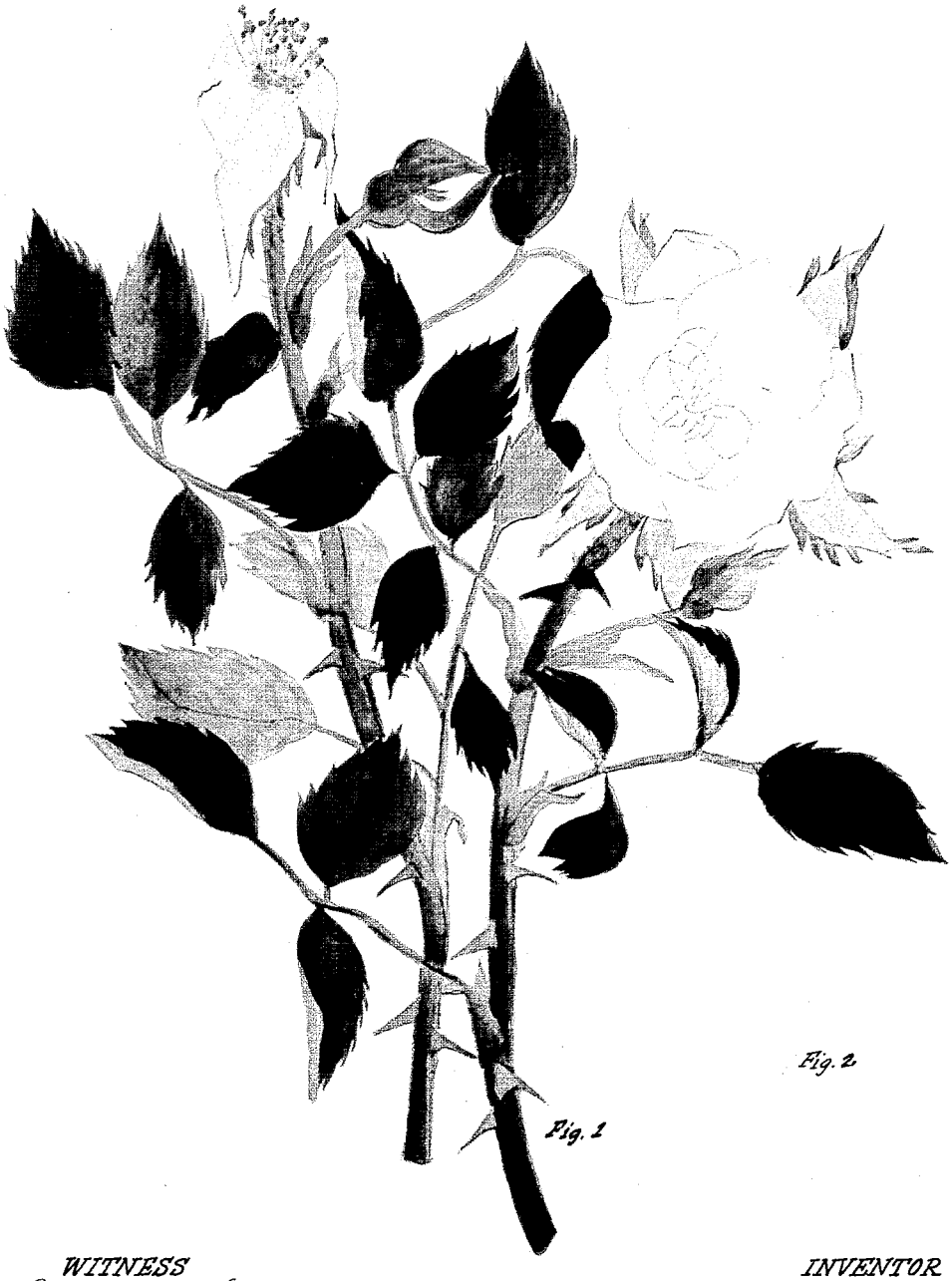

This invention relates to a new and distinct variety of hardy, outdoor climbing hybrid tea rose plant.

This plant is characterized as to novelty by its parentage, its recurrent flowering habit, and its exceedingly large and double flowers.

This variety is unusual in its parentage in that it is a cross of Lulu (hybrid tea, unpatented) and an un-named seedling, which un-named seedling is a cross between *Rosa bracteata* and Guinee (unpatented). *Rosa bracteata* is a species bearing single white flowers, is a very thorny plant and a vigorous climber. It is one parent of the famous rose Mermaid. Guinee is a dark, velvety red, double flowered climbing hybrid tea.

The new variety is recurrent or everblooming in habit, more recurrent than most climbing hybrid tea roses. The flowers are large and very double, with somewhat the appearance of the old "cabbage roses." The flowers always open into a soft, lovely pink shade and are rather spectacular because of their size and extreme doubleness. The new variety will grow into a climber 10–14 feet high. While it may not be dependably hardy in severe climates, in milder areas such as the Pacific coast area, California, Arizona and the gulf, it does very well.

This variety of climbing hybrid tea rose plant was originated by me, in my nursery located at Visalia, California, and under conditions of careful control and observation, by crossing Lulu as the seed parent and an unnamed seedling (*Rosa bracteata*×Guinee) as the pollen parent. Subsequent to origination of the variety, I successfully, asexually reproduced it in my nursery, located as aforesaid, by budding as well as cuttings, the reproductions having run true in all respects.

The drawing illustrates the variety including foliage, buds and flowers.

Referring now specifically to the new and distinct variety of climbing hybrid tea rose plant, the following is a detailed description thereof in outline; all major color plate identifications being to the British Colour Council Horticultural Colour Chart, except where common terms of color definition are employed.

Type: Hardy; climbing; outdoor; seedling; garden decoration.

Class: Climbing hybrid tea.

*Flowers*

Continuity: Intermittent.

Fragrance: Moderate.

Flowers borne: Several to stem in rounded cluster; normal, medium length stems.

Quantity of bloom: Moderate to free, outdoors.

Bud:

*Peduncle.*—Short to medium; medium to heavy; of medium stiffness; medium green; numerous pale green or pinkish prickles.

*Before calyx breaks.*—Size—large. Form—short, pointed, somewhat globular, with foliaceous appendages and moss-like prickles or hairs on the surface of the bud, with stout foliaceous parts extending beyond the tip of the bud equal to ¼ or more of its length. Color—normal green.

*As calyx breaks.*—Color—pink or light reddish.

*As first petal opens.*—Size—large. Form—short, pointed, globular. Color: outside—Phlox Pink (about 625/3); inside—Phlox Pink (about 625/3). Opening—opens slowly.

Bloom:

*Size when fully opened.*—Large, 3½" to 4" and sometimes larger.

*Petalage.*—Very double; from 100 to more petals arranged regularly.

*Form.*—Cupped at first; becoming flat and cupped; petals remaining at first very loosely rolled inward; becoming later, at maturity, flat cupped, with outer petals rolled outward.

Petals: Thin; soft; inside satiny; outside satiny.

*Shape.*—Outside—obovate; apex nearly flat. Intermediate—obovate. Inside—lanceolate.

*Color.*—Newly opened flower from plant grown outdoors (September)—(1) Outside petal: outside surface—Phlox Pink, about 625/3; inside surface—Phlox Pink, about 625/3. (2) Intermediate petal: outside surface—Phlox Pink, about 625/3; inside surface—Phlox Pink, about 625/3. (3) Inner petal: outside surface—Neyron Rose 623/3; inside surface—Neyron Rose 623/3. All petals have a bit of soft yellow at the base shading into yellowish-pink and thence into colors indicated above. Rose opened for three days outdoors—Outside petal: outside surface—Phlox Pink 625/3; inside surface—Phlox Pink 625/3. Inside petal: outside surface—Phlox Pink 625/3; inside surface—Phlox Pink 625/3. The outside petals are sometimes the exact same shade as the inside petals, but more often are a paler shade. There is a tiny touch of pale yellow at all petal bases.

*General color effect.*—Newly opened flower—soft cotton candy pink. Three days open—same only softer.

*Behavior.*—Petals often shed but part may persist; fade into light brown; may ball in in cold, wet weather.

*Flower longevity.*—Three to four days and sometimes longer on bush in garden (June). Two to three days as cut roses grown outdoors and kept at living room temperatures (June).

Reproductive organs:

*Stamens.*—Very few or none.

*Filaments.*—Of medium length if any are present; reddish; no anthers.

*Anthers.*—None.

*Pollen.*—None.

*Pistils.*—Of medium number.

*Styles.*—Even; of medium length; thin; bunched.

*Stigma.*—Yellow.

*Ovaries.*—Enclosed in calyx.

*Hips.*—None.

*Sepals.*—Permanent; of moderate length; spear shaped; recurved; green becoming light brown.

*Seeds.*—None.

*Plant*

Foliage:

*Leaves.*—Compound of 7 leaflets; of normal abundance; medium large; moderately heavy; leathery.

*Leaflets.*—Oval; apex acute; serrate margin.

*Color.*—Mature: upper surface—normal dark green; under surface—normal green. Young: upper surface—glossy light to normal green with bronzed edges; under surface—light to normal green overlaid with bronze.

*Rachis.*—Of medium weight; upper side grooved, hairy; under side sparsely to moderately thorny, with short thorns.

*Stipules.*—Of medium length; of medium width; with short points turning out at an angle of about 45°.

*Disease.*—Subject to mildew in cool, damp weather.

*Growth*

Habit: Climbing; many branches.
Growth: Free vigorous.
Canes: Of medium weight.
Main stems: Gray.
*Thorns.*—Several; of medium length; hooked downward; with moderately short, broad base.
*Prickles.*—None.
*Hairs.*—None.
Branches: Green.
*Thorns.*—Several; of medium length; hooked downward slightly; base oval and moderately small; thorns are slender and come to rather a needle point, especially on young shoots.
*Prickles.*—None.
*Hairs.*—None.
New shoots: Bright green.
*Thorns.*—Several; medium to long; hooked slightly downward; base oval and moderately small; thorns are slender and come to rather a needle point.
*Prickles.*—None.
*Hairs.*—None.

The following is claimed:

A new and distinct variety of climbing hybrid tea rose plant, substantially as herein shown and described, of the hardy, outdoor variety characterized by its recurrent, ever-blooming growth habit which resembles its grandparent *Rosa bracteata*, and by its exceedingly large and double flowers which resemble its grandparent Guinee, said flowers borne several to a stem in a rounded cluster, with the thin, satiny petals of said flowers arranged regularly in quantities of 100 or more to each flower, with newly opened flowers of a soft cotton candy pink shade and flowers opened three days of a softer pink shade.

No references cited.